United States Patent [19]

Miller

[11] Patent Number: 5,749,843

[45] Date of Patent: May 12, 1998

[54] WOVEN OR KNITTED ELASTIC BANDAGES HAVING CONTROLLED COMPRESSIVE FORCES

[75] Inventor: Nigel David Miller, Little Neston, United Kingdom

[73] Assignee: Smith & Nephew Group Research Centre, Henslington, England

[21] Appl. No.: 479,560

[22] Filed: Jun. 7, 1995

Related U.S. Application Data

[63] Continuation of Ser. No. 200,934, Feb. 22, 1994, abandoned, which is a continuation of Ser. No. 75,863, Jun. 11, 1993, abandoned, which is a continuation of Ser. No. 928,543, Aug. 13, 1992, abandoned, which is a continuation of Ser. No. 837,550, Feb. 14, 1992, abandoned, which is a continuation of Ser. No. 476,408, filed as PCT/GB90/00297 Feb. 26, 1990 published as WO90/09770 Sep. 7, 1990, abandoned.

[30] Foreign Application Priority Data

Feb. 25, 1989 [GB] United Kingdom .................. 8904375
Jul. 27, 1989 [GB] United Kingdom .................. 891721

[51] Int. Cl.$^6$ ........................................ A61L 15/00
[52] U.S. Cl. .................. 602/75; 602/42; 602/76; 139/422; 66/192
[58] Field of Search ............................... 602/42, 43, 44, 602/75, 76; 139/422, 426 R; 66/192, 195, 202

[56] References Cited

U.S. PATENT DOCUMENTS

| | | |
|---|---|---|
| 3,523,528 | 8/1970 | Patience et al. |
| 4,024,312 | 5/1977 | Korpman ..................... 128/156 |
| 4,366,814 | 1/1983 | Riedel. |
| 4,414,970 | 11/1983 | Berry ........................ 128/156 |
| 4,653,492 | 3/1987 | Parsons. |
| 4,891,957 | 1/1990 | Strack et al. ................. 66/202 |

FOREIGN PATENT DOCUMENTS 2542201 9/1984 France.

OTHER PUBLICATIONS

*Textile Terms and Definitions*, Ninth Edition—The Textile Institute, 1991, pp. 118, 360, and iii.

*Primary Examiner*—Paul B. Prebilic
*Attorney, Agent, or Firm*—Graham & James LLP

[57] ABSTRACT

An elastic bandage comprises a knitted or woven fabric containing both inelastic and elastic yarns in which the ratio of inelastic yarns to elastic yarns is from 1:1 to 12:1 and in which the bandage achieves an effective compressive force at an extension of between 20 to 60% after which any further extension of the bandage is accompanied by only a small increase in compressive force. Suitable polymers for the elastic yarns include block copolymers such as styrene-butylene-ethylene-styrene block copolymers. Woven or knitted elastic bandages made of such yarns exhibit good stress retention properties.

19 Claims, 3 Drawing Sheets

WOVEN OR KNITTED ELASTIC BANDAGES HAVING CONTROLLED COMPRESSIVE FORCES

This application is a continuation of Ser. No. 08/200,934 filed Feb. 22, 1994 and now abandoned which is a continuation of Ser. No. 08/075,863 filed Jun. 11, 1993 and now abandoned which is a continuation of Ser. No. 07/928,543 filed Aug. 13, 1992 and now abandoned which is a continuation of Ser. No. 07/837,550 filed Feb. 14, 1992 and now abandoned which is a continuation of Ser. No. 07/476,408, filed as PCT/GB90/00297 Feb. 26, 1990 published as WO90/09770 Sep. 7, 1990 and now abandoned.

The present invention is concerned with woven or knitted elastic compression bandages.

Woven or knitted elastic bandages in both adhesive and non-adhesive forms are used to provide support, to assist in the healing of strained muscles and in the treatment of various venous conditions. Conventional elasticated woven or knitted bandages have one or more warp yarns which comprise elastomeric materials such as natural rubber or synthetic elastomeric materials such as polyurethane. It is important that these bandages are applied at the correct tension which is sufficiently high to enable them to maintain an effective level of compressive force under the bandage over a period of time.

However, a disadvantage associated with the known woven or knitted bandages is that if they are stretched too much during the application, the compression force under the bandage may be overly great and cause damage, for example by restriction of the blood supply.

We have now found that the disadvantages of the prior art bandages can be alleviated by the provision of a woven or knitted elastic bandage which generates the required compressive force at low extensions. This bandage is in the form of a knitted or woven fabric which contains both elastic and inelastic yarns and which shows a large rate of increase in compressive force with extension at low extensions until an extension is reached after which the force increases only slightly even though there might be a large increase in extension. This extension is reached at between 20% and 60% extension and provides an effective compressive force. These bandages therefore provide a safe and effective compressive force at lower extension than has previously been possible with knitted or woven bandages which makes the bandage easier to apply. Since any further increase of the compressive force after this extension is only slight even for large extensions it means these bandages are also safer to apply. It is also advantageous that these bandages require less elastic material so a thinner, less bulky bandage is achieved. Due to the woven or knitted nature of the bandage the yarns move over each other on extension thereby avoiding any strain between the elastic material and inelastic material which had been found in some earlier bandages.

Accordingly the present invention provides an elastic bandage which comprises a knitted or woven fabric containing both inelastic and elastic yarns in which the ratio of inelastic yarns to elastic yarns is from 1:1 to 12:1 and in which the bandage achieves an effective compressive force at an extension of between 20 to 60% after which any further extension of the bandage is accompanied by only a small increase in compressive force.

When subjected to extension all woven and knitted bandages will extend until the point where lock-out occurs. 'Lock-out' is the point where the bandage cannot undergo any further extension without causing damage to the fabric of the material. The term 'further extension' as used herein refers to extension until 'lock-out' occurs.

Figure 1:
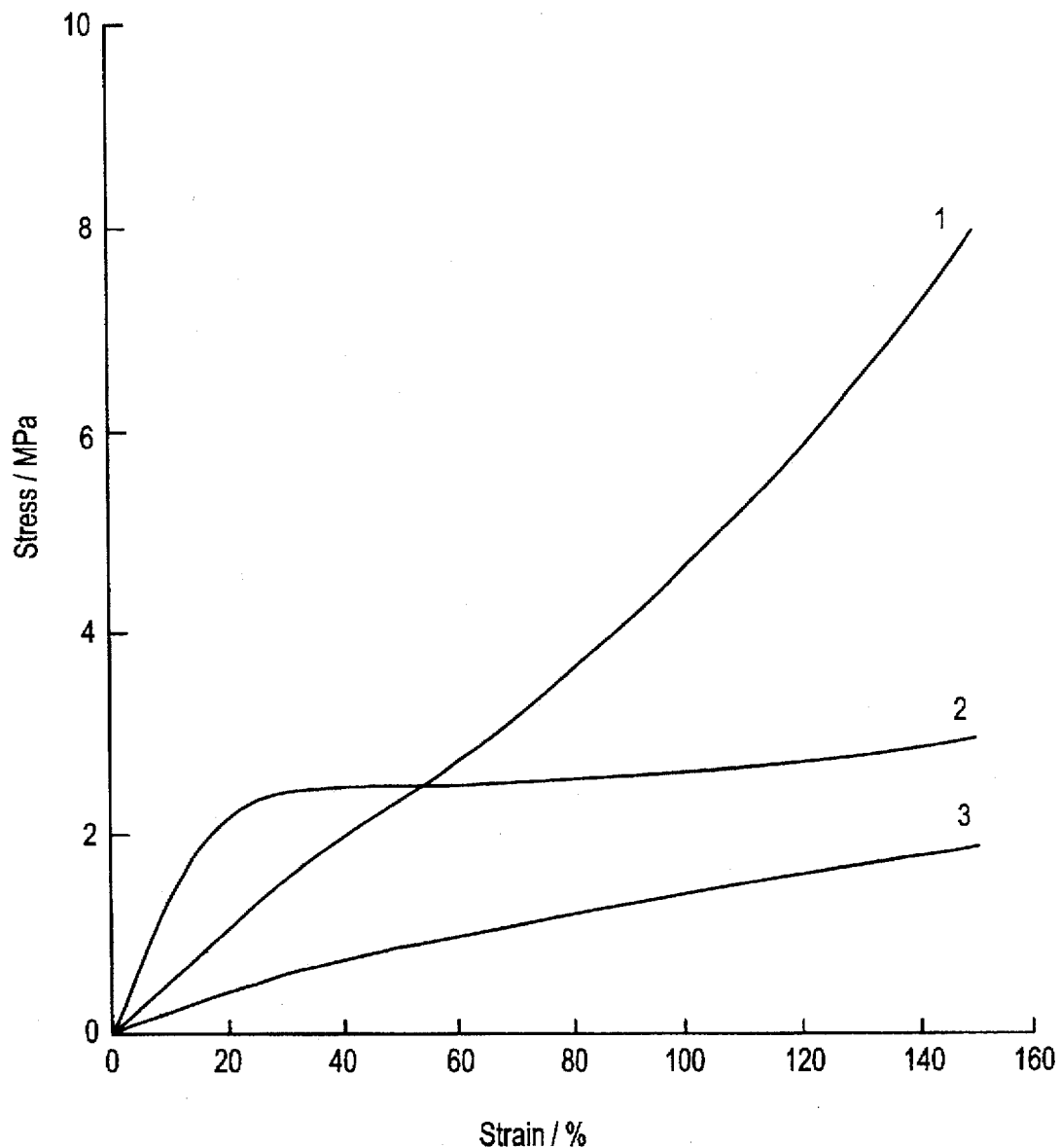
FIG. 1 shows the results of change in stress with elongation. Curve 1 shows the stress-strain data for a LYCRA bandage. Curve 2 shows the data for a bandage according to the present invention. Curve 3 shows the data for a bandage made of natural rubber filaments.

The synthetic elastomeric polymers empolyed in the present inventon are aptly block copolymers. The synthetic elastomeric polymers employed in the present invention are more aptly tri-block copolymers.

The synthetic elastomeric polymers employed in the present invention preferably contain hard-blocks and soft-blocks.

Favoured tri-block copolymers are those of the type known as, A—B—$A^1$ copolymers in which most favourably the A and $A^1$ blocks are the same.

In such copolymers the A-block and the $A^1$-block as hard blocks and are derived from materials which have a sufficiently high glass transition temperature to form crystalline or glass domains at the working temperature of the polymer. Such hard blocks generally perform the function of agglomerating strongly with other hard blocks in the polymer mass. Suitable polymers for such hard blocks include essentially hydrocarbon materials. Styrene, alpha methyl styrene and substituted styrenes are particularly suitable hard blocks.

The material forming the B-block will have sufficiently low glass transition temperature at the working temperature of the polymer such that crystalline or glassy domains are not formed at these working temperatures. The B-block may thus be regarded as a soft block.

Apt materials for forming the soft B-blocks include polymers which are essentially hydrocarbon such as polymers derived from alkenes or alkdienes, especially those of 2 to 4 carbon atoms such as butadiene, ethylene, isoprene and butylene. Preferred hydrocarbons are those which are saturated. The more preferred soft blocks have at least two dissimilar components, such as those polymers based on ethylene-butylene.

Use of such preferred components has lead to bandages having the desirable properties described hereinafter.

The block copolymers for use in the invention may be prepared by conventional anionic polymerisation techniques and suitable materials are available.

Suitable block copolymers for use in the present invention include styrene-butadiene-styrene block copolymers such as those which are available commercially as CARIFLEX (Trade mark). A suitable grade of CARIFLEX is TR 1102. Other block copolymers include styrene-isoprene-styrene block copolymers, for example, that sold under the trade name CARIFLEX TR 1107.

Preferred block copolymers for use in the present invention are styrene-ethylene-butylene-styrene block copolymers. Such block copolymers are available commercially from Shell Chemical Company and sold under the trade names Kraton G27, KRATON G1650, Kraton G1651 and KRATON G1652. It follows that a preferred embodiment of the invention provides an elastic bandage which comprises a knitted or woven fabric containing both inelastic and elastic yarns in which the elastic yarns comprise a styreneethylene-butylene-styrene block copolymer and in which the ratio of inelastic yarns to elastic yarns is from 1:1 to 12:1 and in which the bandage achieves an effective compressive force at an extension of between 20 to 60% after which any further extension of the bandage is accompanied by only a small increase in compressive force.

The block copolymers may be employed as a block copolymer, a blend of block copolymers, or a blend of one or more block copolymers with one or more other polymers such as polypropylene. The block copolymers employed preferably only have minor quantities of, and most preferably essentially no, such other polymers present.

Suitable blends include blends of styrene-ethylene-butylene-styrene copolymer grades of different molecular weight such as 1:1 mixtures of KRATON G1650 and KRATON G1652 or a mixture of 9 parts of KRATON G1650 with 1 part of G1651, and blends of styrene-ethylene-butylene-styrene block copolymers with up to 30% by weight of polypropylene, for example from 5 to 20% by weight of polypropylene.

The block copolymers for use in the present invention may be blended with other additives in order to aid processing, for example extrusion, of the polymer.

The relationship between the force and extension of a bandage of the invention may be illustrated by taking a sample of the bandage and stretching it using an Instron Tensile Testing Machine (Instron is a trade mark) and representing the results graphically. At low extensions the rate of increase of the compressive force with extension is large as shown by a steep slope to the graph, until an extension is reached at which the slope of the graph abruptly changes to a shallow, almost horizontal slope. This shows that any further extension of the bandage is accompanied by only a small increase in force. The extension at which this abrupt change of slope occurs is suitably from 20% to 60% extension, is more suitably 20% to 50% and is preferably 25% to 45%; for example 25%, 30%, 40% and 45%. This amount of extension provides the desired magnitude for the compressive force. The low value for the extension as compared to previously known bandages means that the bandage is easier to apply since it does not have to be extended so much and also any over extension causes only a slight, if any, increase in the compressive force so the bandage is safer to apply.

Typically the bandage of the invention may be extended by up to 100% with only a minimal, if any increase in compressive force.

The present invention also provides an elastic yarn which is suitable for use in elastic bandages, which yarns comprises at least one filament of an elastomeric polymer wherein the filament exhibits a stress of at least 0.8 MPa at an extension of 20%, a stress at 100% extension which is not more than 0.5 MPa greater than the stress at 60% extrusion, and a retained stress of more than 60%.

The stress values at 20%, 60% and 100% extension are determined by stretching the filament at 300 mm/min at 20° C. using an INSTRON Tensile Testing Machine and measuring the stress (expressed in megapascals - MPa) at the selected extensions.

The preferred A—B—A$^1$ polymers hereinbefore described, especially those having a soft block containing more than one component are particularly suitable yarns.

In order for bandages of the invention to provide an effective compressive force with the minimum of extension, it is desirable that it and the elastic filaments from which it is comprised should have a high stress (or compressive force) value at 20% extension. Aptly at this extension, the stress values should be at least 1, suitably at least 1.5 and preferably greater than 2 MPa.

Once an effective compressive force has been applied the increase in compressive force with extension should be as small as possible. Thus with bandages of the invention the increase in stress (compressive force) should be no than 0.5 MPa over the 60%–100% extension range. Suitably the stress, for a extension between 60 to 100% will be less than 0.4 MPa (i.e. less than 40%, <0.4/1.0×100=40%) preferably not more than 0.25 MPa and typically less than about 0.15 MPa. (For comparison it may be noted that for bandages employing natural rubber the change in stress between 60% and 100% is about 0.5 MPa although the 20% extension value is only 0.41 MPa. Bandages employing polyurethane (LYCRA) filaments have a change in stress for 60% to 100% extension of 1.6 MPa).

The elastic yarns in accordance with the invention and for use in preferred woven or knitted bandages of the invention are formed from synthetic elastomeric polymers having a force-extension relationship which follows a similar pattern to that of the bandage. The force-extension relationship of such polymers may be measured by stretching a sample of the polymer using an INSTRON Tensile Testing Machine (Instron is a trade mark) and representing the results graphically. As with the bandage the graph shows two regions. In the first region, at low extensions of the elastomeric polymer the rate of increase of the force with extension is large and the slope of the graph is steep. This continues until an extension is reached when the the slope of the graph changes abruptly and further large extensions are accompanied by only small, if any, increases in force. This is shown by the slope of the force-extension curve becoming shallow and even almost horizontal. Therefore suitable elastomeric polymers for use in this invention can have a force-extension relationship, when represented graphically, comprising a steep slope up to from 20% to 60% extension but to have a shallow linear slope above the extension at which the abrupt change in the slope of the graph occurs.

The use of synthetic elastomeric polymers possessing this property prevents a woven or knitted bandage being applied at too large a tension so that the bandage may be applied safely by even an unskilled person. It has been found that the actual value of the sub-bandage compressive force provided by a bandage of the invention can be varied according to the weight per unit area of the elastomeric polymer present in the bandage. Aptly, the sub-bandage compressive force provided by the bandage of the invention will be less than 90 mmHg. Suitable sub-bandage compressive forces provided by the bandages of the present invention can be in the range from 20 to 70 mmHg and preferably 30 to 60 mmHg. The force-extension relationship of the elastomeric polymer used in the bandage effectively means that once a bandage has been selected to give a desired sub-bandage compressive force it cannot be incorrectly applied resulting in a too high a force. Previously if a compressive force at the top end of the range was required, there was a risk of over extending the bandage thereby causing a severe constriction around the limb which is not desirable.

Preferably the elastomeric polymers, employed in bandages and yarns of the invention (for example styrene-ethylene-butylene-styrene block copolymers or related A—B—A$^1$ polymers containing soft blocks of more than one component) are those which show low degrees of stress softening. This may be measured on a sample of the polymer by cycling the polymer between 0 and 300% of its orginal length 10 times. The stress-strain curves were recorded for the first, second and tenth cycles. The stress softening was expressed as a percentage reduction of stress at any given extension in relation to the first cycle. The lower the stress softening the more the bandage may be repeatedly used without loss of its compression properties. Filaments formed from preferred polymers, such as the styrene-ethylene-butylene-styrene and related block copolymers, will exhibit stress softening of less than 30%. This value is expressed as the percentage difference in the stress values at 100% extension between the first and average of the second and tenth cycles. Bandages having such properties are a preferred and highly surprising aspect of this invention.

Favoured polymers used in this invention show a low degree of tensile set. This may be measured on a sample of the polymer using a method described in ASTM D412-87. This involves stretching a dumb-bell-shaped sample of the polymer to 50, 100, 200 or 300% extension at a rate of 200 mm/min. The sample was held at this extension for 10 minutes before the stretch was removed also at 200 mm/min. The samples were released and allowed to rest for 5, 10, 20 or 30 minutes respectively. At the end of the rest period the amount of permanent set was recorded. Preferred polymers showed a low degree of permanent set less than 15% eg. 5% (at 100% extension) which is advantageous when used as a yarn in a bandage.

Yarns made from styrene-ethylene-butylene-styrene and related block copolymers exhibit the property of good stress relaxation. Bandages made of many elastomeric materials will become less stressed with time whilst maintained at fixed extension. Thus although the bandage is not stretching (extending) the compressive force (stress) reduces with time. The yarns and bandages of the present invention suitably have a retained stress of more than 60% whilst maintained at 50% extension at 20° C. for 15 hours, and preferably the retained stress will be greater than 70%. Bandages having such properties are a preferred and highly surprising aspect of this invention.

The use of styrene-ethylene-butylene-styrene and related block copolymers allows woven or knitted bandages to be stressed and relaxed many times without detriment to its elastic or compressive properties.

It is one of the great advantages of the preferred aspects of the present invention that woven or knitted compression bandages may be produced that have a combination of such desirable properties as not only the ability to achieve effective force at low extensions, minimal increase of forces at greater extension but also the ability to retain compressive forces over long periods.

The ability of woven or knitted bandages, made from such polymers, to apply effective compressive forces over small extensions, to have minimal increases in the compressive force under highly extended conditions and to possess high stress retentions (ie. maintenance of the compression force) represents a significant advance in the field of woven or knitted bandages.

The elastic yarn can be either a monofilament or a multifilament yarn. It is preferred to use monofilament yarns which are more robust and easier to weave or knit. However, if the filaments are fine then a multifilament yarn may be used to provide the necessary weight of elastic yarn and to facilitate manufacture of the fabric.

The elastic yarn can suitably be made by extrusion.

When used as a monofilament yarn the elastic yarn can be circular in cross-section and will normally have a diameter of greater than 0.1 mm eg. from 0.1 to 1 mm and preferably from 0.2 to 0.5 mm. If a greater weight of elastic yarn is required in a bandage then two or more of these elastic yarns may be used together. If a multifilament yarn is used then individual filaments can be finer than the monofilaments described above.

The ratio of inelastic to elastic yarns may vary depending on the nature of the fabric, that is whether it is knitted or woven, but generally the ratio can be between 1:1 and 12:1. Values of from 2:1 to 4:1 are found with knitted fabrics and values of 5:1 to 8:1 found with woven fabrics. It is surprising that ratios in this range provide the desired range of compressive force without causing local constrictions or inadequate elastic properties.

The elastic bandage may be in the form of a woven or knitted fabric. Woven fabrics may have any of the weaving patterns which are conventionally used for making elastic bandages. The woven fabric comprises warp and weft threads. The elastic yarn can be present in the warp wherein a proportion of the warp threads are elastic yarn. Thus depending upon the weight of elastomeric polymer required in the bandage every 2nd, 3rd, 4th, 5th etc. warp thread may be an elastic yarn. Suitably the elastic yarn is woven into the fabric under tension and the woven material is allowed to relax. When in use the bandage is re-extended and applied to the affected part it provides the required compressive force.

The knitted fabrics may be in the form of conventional linear bandages or of tubular bandages. When a linear bandage is required the fabric can be in the form of a warp knitted fabric, for example one based on a 3- or 4-bar Raschel knitting pattern. The knitting of the yarns may be arranged so that bar 1 forms the chain stitches from the ground yarn, usually a cotton or cotton/viscose yarn and bars 2 and 3 lay in a ground yarn and the elastic yarn respectively. Aptly the knit has about 80 to 120 wales/10 cm width and 120 to 160 courses /10 cm length. The weight of the fabric may be altered in a conventional manner such as by changing the thickness of the yarn or changing the number of needles over which bar 2 inlays the ground yarn. In another pattern, the knitting of the yarns may be arranged so that bar 1 knits the chain stitches from the elastic yarn and the ground yarns are inlaid from the other guide bars.

Tubular bandages may be knitted on a conventional circular knitting machine. The elastic yarn can be knitted into the bandage in various ways, for example, if the elastic yarn forms the stitches then a tubular bandage is formed which has two-way stretch characteristics or the elastic yarn may be laid into the bandage so as to provide only radial stretch. The ground yarn in tubular bandages may be a cotton or cotton/viscose. The ratio of elastic yarn to ground yarn can suitably be in the ratio of 1:2 to 1:4.

The invention will now be illustrated by the following Examples.

EXAMPLE 1

A styrene-butadiene-styrene elastomer available as KRATON G 27 was extruded into the form of a filamentary yarn. This yarn together with a textured nylon 6.6 yarn was woven into a plain weave with the nylon and KRATON yarns running in the warp direction. The weft was cotton. The bandage comprised 70 nylon ends and 11 KRATON ends in a width of 5.4 cm. The first end was a KRATON yarn and then every 8th end after that was a KRATON yarn with 7 ends of nylon in between. The KRATON yarn was fed in from a beam under tension and the resulting woven bandage allowed to relax when removed from the loom. This bandage when applied to a limb at 30% extension caused a compressive force on the limb of 30 mmHg.

Similar plain weave bandages could be made in which a KRATON yarn was present at every 2nd, 3rd, 4th end etc.

EXAMPLE 2

A bandage was prepared as a plain weave bandage in a similar manner to that described in Example 1 except that a double KRATON yarn was used at each 8th end. In this case the bandage when applied to a limb at 30% extension caused a compressive force on the limb of 60 mmHg.

EXAMPLE 3

A machine capable of carrying out a 3 bar Raschel knitting pattern was used to prepare a warp knitted bandage including Kraton yarn. In the three bar knitting pattern, bar 1 performs a simple chain stitch and bars 2 and 3 perform lapping motions to lay in the other yarns. Bar 1 is used to form chain stitches from a ground yarn such as a cotton/viscose yarn. Bar 2 carries a similar yarn and Bar 3 carries the elastomeric yarn. A suitable knit has 94 wales/10 cm (approx) and 140 courses/10 cm. The weight of the fabric may be altered by changing the number of needles over which bar 2 inlays the cotton/viscose ground yarn.

EXAMPLE 4

A machine capable of knitting a four bar Raschel knit was used to prepare a knitted elastic bandage containing the elastomeric yarn. The elastomeric yarn may be knitted on bar to form the chain stitches instead of in laid as in Example 3. The cotton/viscose ground yarns may be introduced on bars 2, 3 and 4.

EXAMPLE 5

Figure 3:
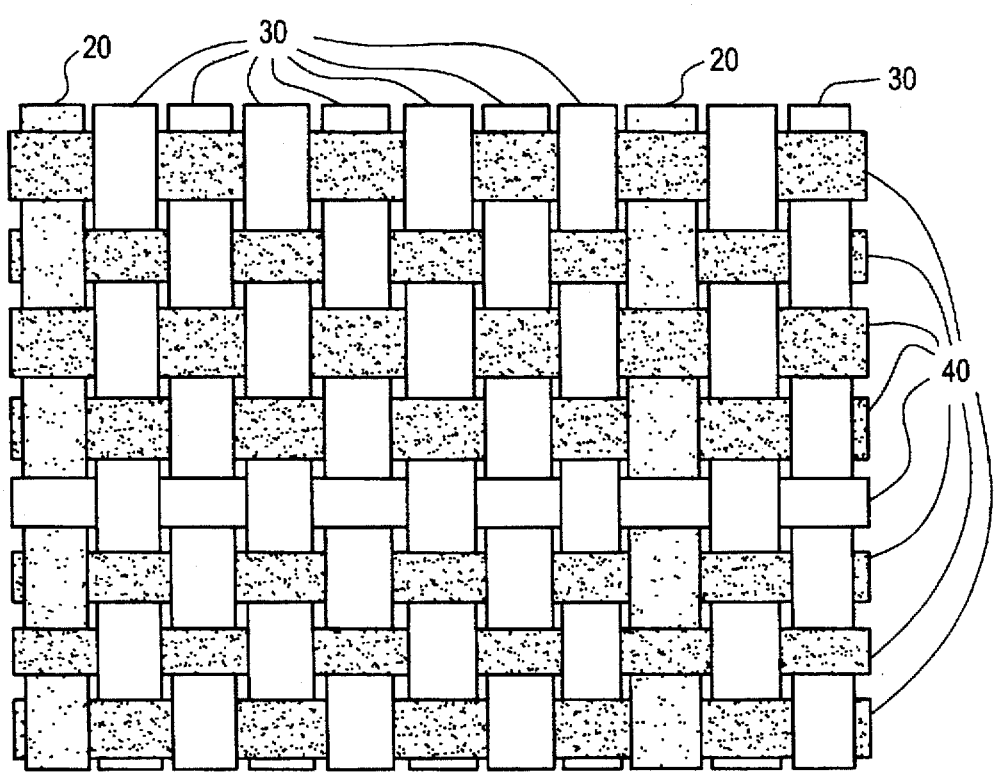
FIG. 3 shows the fibers in a bandage made according to the present invention.

A circular knitting machine was used to form a tubular bandage incorporating the elastomeric yarn. The elastomeric yarn may be incorporated in one of two ways. Firstly if the yarn forms the stitches then a tubular bandage is formed which has two-way stretch characteristics. Secondly the elastomeric yarn may be laid into the knitted tube. In this case the ground yarn is either cotton or viscose and has a weight per unit length of 268 d/tex. A suitable circular knitting machine has 200 cylinder needles and 200 dial needles. In a suitable bandage there are 14 to 21 courses per 2.5 cm and the ratio of elastomeric yarn to spun yarn threads may be 1:2 or 1:4. FIG. 3 exemplifies a fabric 1 made in accordance with Example 1, with Kraton filaments 20, with elements 30 of nylon 6.6 and cotton elements 40.

EXAMPLE 6

100 parts by weight of styrene-ethylene-butylene-styrene copolymer (KRATON G1650—Shell Chemicals) were compounded with 1 part by weight of each of Glyceryl Mono-Stearate and Irganox 1010 and extruded using a Brabender Extruder into 0.6 mm diameter filaments.

The filaments were coated with talc and beamed onto a small beamette which was mounted in a beam holder behind the narrow loom of the main beamer. The main beam contained a textured nylon (available from Norfold Textured Yarns).

The weft yarn was a $16^5$ cotton yarn (available from UCO Yarns S.A.).

The yarns were woven into a plain weave fabric in which the ratio of inelastic (nylon) to elastic (KRATON) yarns was 5:1. The fabric had 120 ends of nylon and 25 ends of KRATON.

The effective compressive force of the bandage when applied to a limb occurs at an extension of about 30%.

A sample of the formed bandage was then subject to a stress-strain test in which the bandage was extended to 140%. The results of change in stress with elongation is shown in FIG. 1 of the accompanying drawings (Curve 2). Curve 1 shows the stress-strain data for a commercially available bandage made from polyurethane filaments sold under the name Lycra (E. I. Dupont) and curve 3 shows the stress-strain characteristics of a bandage using natural rubber filaments.

Figure 2:
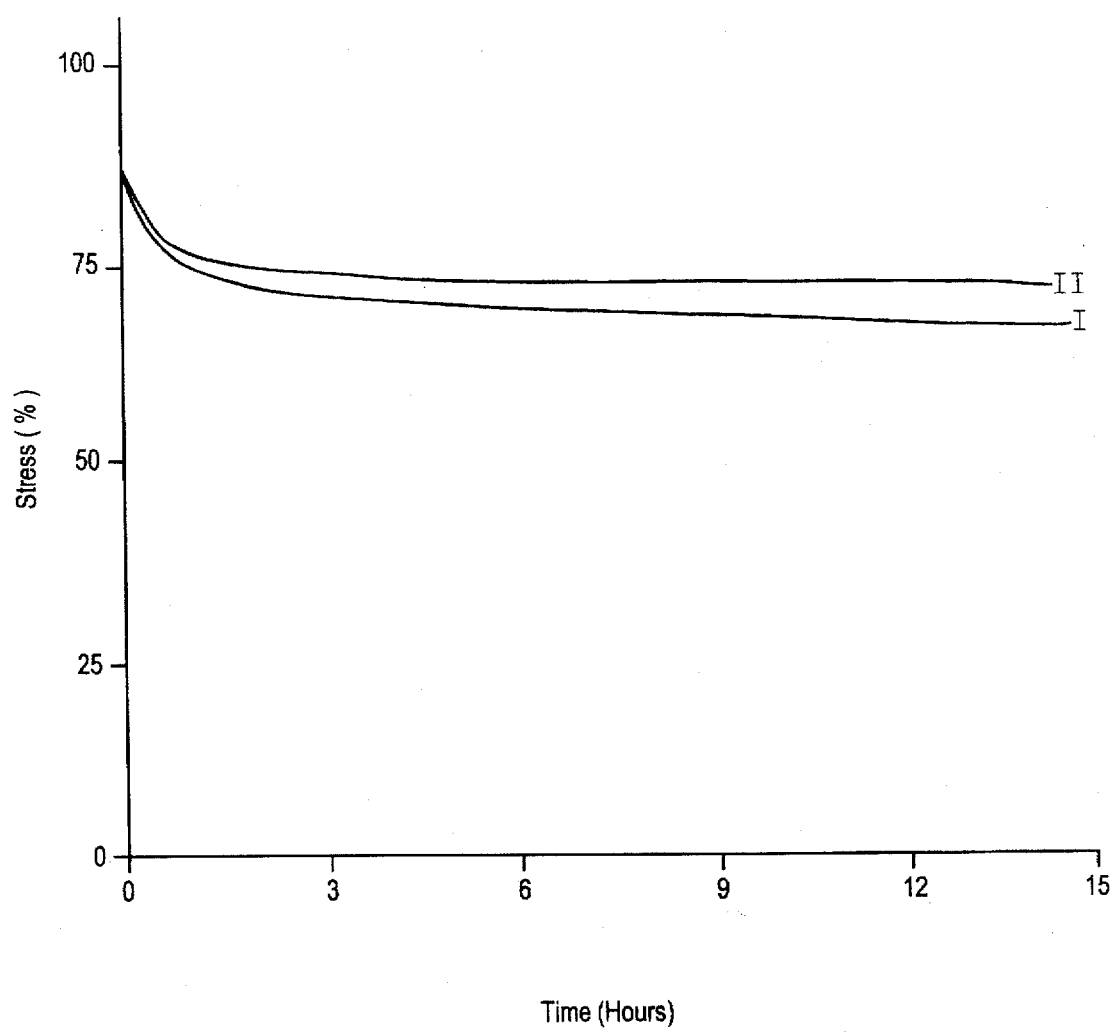
FIG. 2 shows the stress retention value for Curve I for a bandage according to the present invention. Curve II shows it for a LYCRA bandage.

FIG. 2 illustrates the stress retention values for a bandage of the invention (Curve I) and a prior art Lycra filament bandage (Curve II).

It will be seen that the woven bandage of the invention possess both good stress-retention and good effective compression after a small extension with minimal increase in stress over larger extensions.

I claim:

1. An elastic bandage comprising a knitted or woven fabric containing both inelastic and elastic yarns, knitted or woven together, in which the ratio of inelastic yarns to elastic yarns is from 1:1 to 12:1 and in which the bandage achieves an effective compressive force at an extension of between 20 to 60% after which any further extension of the bandage up to 100% is accompanied by an increase of less than 40% in compressive force above the effective compressive force.

2. A bandage as claimed in claim 1 wherein the elastic yarn comprises a synthetic elastomeric polymer.

3. A bandage as claimed in claim 2 wherein the elastomeric polymer is a single block copolymer, a blend thereof with another block copolymer, or a blend of at least one block copolymer and another polymer.

4. A bandage as claimed in claimed 3 wherein the single block copolymer and the one block copolymer are triblock copolymers of the type A—B—$A^1$ wherein $A^1$ and A may be the same or different and are polymers derived from styrene, alpha, methyl styrene, or a substituted styrene and B is a polymer derived from an alkene or alkdiene having 2 to 4 carbon atoms.

5. A bandage as claimed in claim 2 wherein the synthetic elastomeric polymer is a styrene-butadiene-styrene block copolymer.

6. An elastic bandage which comprises a knitted or woven fabric containing both inelastic and elastic yarns, knitted or woven together, in which the elastic yarn is formed from a styrene-ethylene-butylene-styrene block copolymer in which the ratio of inelastic yarns to elastic yarns is from 1:1 to 12:1 and in which the bandage achieves an effective compressive force at an extension of between 20 to 60% after which any further extension of the bandage up to 100% is accompanied by an increase of less than 40% in compressive force above the effective compressive force.

7. An elastic bandage as claimed in claim 1 wherein the effective compressive force ranges from 2.7 to 9.3 kPa.

8. A bandage as claimed in claim 1 wherein the effective compressive force is at from 25 to 45% elongation.

9. A bandage as claimed in claim 2 in which the elastomeric polymer has a degree of stress softening of less than 30%.

10. A bandage as claimed in claim 2 in which the elastomeric polymer has a degree of permanent set of less than 15%.

11. A bandage as claimed in claim 1 wherein the elastic yarn has a retained stress of at least 60% while maintained at 50% extension at 20° C. for 15 hours.

12. A bandage as claimed in claim 1 wherein the elastic yarns are yarns having a cross-sectional diameter of more than 0.1 mm.

13. A bandage as claimed in claim 12 wherein the elastic yarns have a cross-sectional diameter of from 0.1 to 1 mm.

14. A bandage as claimed in claim 1 in which the bandage is a knitted fabric and the ratio of inelastic yarn to elastic yarn is from 2:1 to 4:1.

15. A bandage as claimed in claim 1 in which the bandage is a woven fabric and the ratio of inelastic yarns to elastic yarns is from 5:1 to 8:1.

16. A bandage as claimed in claim 1 in which the elastic yarns provide a stress of at least 0.8 MPa at an extension of 20%, a stress at 100% extension which is no more than 0.5 MPa greater than the stress at 60% extension and a retained stress of more than 60%.

17. A bandage as claimed in claim 16 wherein the stress exhibited by the elastic yarns at 20% extension is at least 1.5 MPa.

18. A bandage as claimed in claim 16 wherein the stress exhibited by the elastic yarns at 100% elongation is not more than 0.25 MPa greater than at 60% extension.

19. A bandage as claimed in claim 1, wherein effective compression force ranges from 4.0 to 8.0 kPa at an extension of from 20 to 60%.

* * * * *

UNITED STATES PATENT AND TRADEMARK OFFICE
CERTIFICATE OF CORRECTION

PATENT NO. : 5,749,843  
DATED : May 12, 1998  
INVENTOR(S) : Nigel D. Miller

Page 1 of 1

It is certified that error appears in the above-identified patent and that said Letters Patent is hereby corrected as shown below:

Title page,
Item [73], Assignee, please delete [Smith & Nephew Group Research Centre, Henslington, England] and please insert -- Smith & Nephew PLC, London, England --

Signed and Sealed this

First Day of January, 2002

Attest:

Attesting Officer

JAMES E. ROGAN  
*Director of the United States Patent and Trademark Office*